(12) United States Patent
Hafiz et al.

(10) Patent No.: US 10,556,114 B2
(45) Date of Patent: Feb. 11, 2020

(54) IMPLANTABLE MEDICAL DEVICE HOUSING HAVING POLYMER COATING

(71) Applicant: Heraeus Deutschland GmbH & Co. KG, Hanau (DE)

(72) Inventors: Jami A. Hafiz, Cedar Park, TX (US); Jeremy Glynn, Buffalo, MN (US); Steven Harein, Mahtomedi, MN (US)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 75 days.

(21) Appl. No.: 15/542,378

(22) PCT Filed: Jan. 8, 2015

(86) PCT No.: PCT/US2015/010630
§ 371 (c)(1),
(2) Date: Jul. 7, 2017

(87) PCT Pub. No.: WO2016/111690
PCT Pub. Date: Jul. 14, 2016

(65) Prior Publication Data
US 2017/0368356 A1    Dec. 28, 2017

(51) Int. Cl.
*A61N 1/375*    (2006.01)
(52) U.S. Cl.
CPC .................... *A61N 1/375* (2013.01)
(58) Field of Classification Search
CPC ..... A61N 1/375; A61N 1/3756; A61N 1/3968
See application file for complete search history.

(56) References Cited

U.S. PATENT DOCUMENTS

| | | | |
|---|---|---|---|
| 5,925,069 A | 7/1999 | Graves et al. | |
| 6,295,474 B1* | 9/2001 | Munshi | A61N 1/375 607/120 |
| 2005/0004620 A1 | 1/2005 | Singhal et al. | |
| 2007/0128420 A1* | 6/2007 | Maghribi | A61L 27/48 428/221 |
| 2010/0278895 A1* | 11/2010 | Burgmeier | A61L 27/18 424/423 |
| 2011/0021899 A1* | 1/2011 | Arps | A61K 9/0009 600/372 |
| 2013/0238085 A1* | 9/2013 | Nabutovsky | A61L 29/16 623/1.42 |
| 2015/0238770 A1* | 8/2015 | Dorman | A61N 1/3758 607/115 |

OTHER PUBLICATIONS

International Search Report and the Written Opinion for International Application No. PCT/US2015/010630 dated Sep. 11, 2015 (11 pages).

* cited by examiner

*Primary Examiner* — Paula J Stice
(74) *Attorney, Agent, or Firm* — Dicke, Billig & Czaja, PLLC

(57) ABSTRACT

One aspect provides a housing for an implantable medical device, the housing including a metal substrate having an external surface, and a polymer coating disposed on the external surface of the metal housing, the polymer coating comprising at least one layer of polymer material.

12 Claims, 7 Drawing Sheets

IMPLANTABLE MEDICAL DEVICE HOUSING HAVING POLYMER COATING

CROSS REFERENCE TO RELATED APPLICATION

This Utility Patent Application claims the benefit of the filing date of International Application No. PCT/EP2015/010630, filed Jan. 8, 2015, which is herein incorporated by reference.

BACKGROUND

Implantable medical devices, such as cardiac pacemakers, cardiac defibrillators, and neurostimulators, receive and/or deliver electrical signals to/from portions of the body via sensing and/or stimulating leads. Implantable medical devices typically include a metal housing (e.g. titanium) having a hermetically sealed interior space which isolates the internal circuitry, connections, power sources, and other device components from body fluids. A feedthrough device, or feedthrough, establishes electrical connections between the hermetically sealed interior space and the exterior bodily fluid side of the device.

Handling during manufacturing processes can damage the surfaces of the metal housings. If not addressed, scratches and abrasions to the housing surfaces decrease lubricity of the implantable medical device which can result in damage to bodily tissue during implantation, and which can result in poor housing-tissue interface after implantation. Poor housing tissue-interface can, in-turn, increase interfacial impedance and adversely impact the electrical characteristics of the housing (such as when the housing serves as an anode in unipolar systems, for example). If the damage is severe enough, the housing must be discarded, thereby reducing manufacturing yield.

To address these issues, an intense visual inspection is performed on each housing component throughout the course of the manufacturing process, with damage to the housings being repaired, when possible, through manual buffering and polishing processes. Such techniques are expensive and slow the manufacturing process.

For these and other reasons there is a need for the embodiments of the present disclosure.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
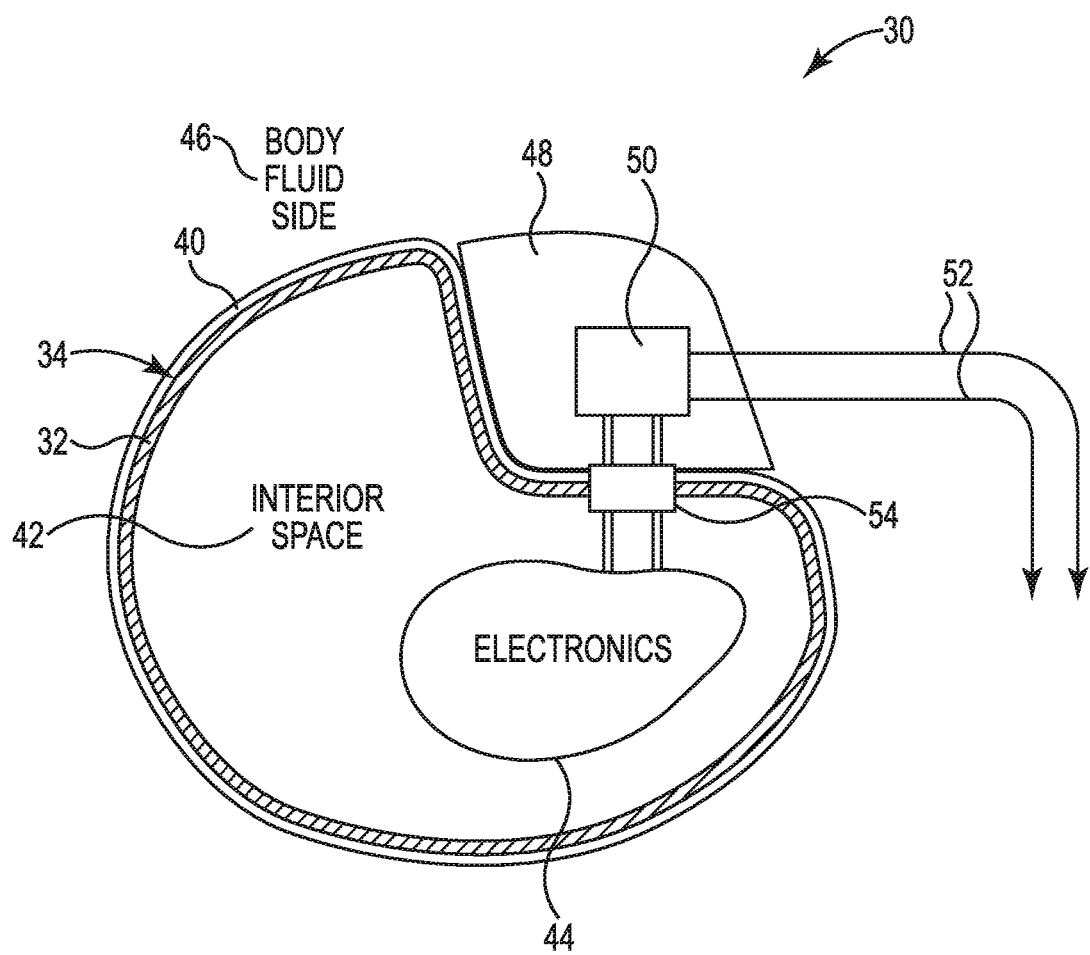
FIG. 1 is a block and schematic diagram generally illustrating an example of an implantable medical device including a housing having a polymer coating according to one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

One embodiment is a housing for an implantable medical device that includes a metal substrate having an external surface. A polymer coating is disposed on the external surface of the metal housing, the polymer coating comprising at least one layer of polymer material. In some embodiments, the polymer coating provides beneficial properties to the metal housing, including improved tissue interface after implantation, enhanced tissue-electrode interface, and improved anti-static properties. In some embodiments, the polymer coating reduces wear, tear and scratches on the exterior surface during handling and assembly of the housing, thereby avoiding the need for buffing. In some embodiments, the polymer coating provides antimicrobial benefits, and in others provides a very low friction surface.

In one embodiment, the polymer coating includes a single layer of a polymer material disposed directly on the external surface of the metal substrate. In another embodiment, the single layer of polymer material includes a conductive polymer material. In one embodiment, the single layer of polymer material includes a dissolvable polymer material. In one embodiment, the single layer of polymer material includes a dissolvable scratch resistant polymer material. In one embodiment, the single layer of polymer material includes a dissolvable antimicrobial polymer material. In one embodiment, the polymer coating includes a multilayer coating having multiple layers of polymer material. In one embodiment, the polymer coating includes a first layer of polymer material disposed directly on the exterior surface of the housing, and one or more second layers of polymer material disposed on the first layer of polymer material. In one embodiment, the first layer of polymer material includes a conductive polymer material, and each of the one or more second layers of polymer materials include dissolvable polymer materials each being configured to dissolve at different rates under different conditions. In one embodiment, the first layer of polymer material and each of the one or more second layers of polymer materials include dissolvable polymer materials, and each of first layer and one or more second layers are configured to dissolve at different rates under different conditions. In some embodiments, the polymer coating provides beneficial properties to the metal housing, including improved tissue interface after implantation, enhanced tissue-electrode interface, improved anti-static properties, reduced wear, tear and scratches on the exterior surface during handling and assembly of the housing, antimicrobial benefits and very low friction surface.

One embodiment is an implantable medical device including a metal housing defining an interior space and having an external surface. A polymer coating is disposed on and covering the external surface of the metal housing, the polymer coating including at least one layer of polymer material.

In one embodiment, the polymer coating comprises a single layer of a dissolvable polymer disposed directly on the external surface of the metal housing. In one embodiment, the polymer coating includes a first layer of conductive polymer disposed directly on the external surface of the metal housing. In one embodiment, the polymer coating includes a second layer of a dissolvable polymer disposed directly on the first layer of conductive polymer. In one embodiment, the second layer of dissolvable polymer includes an antimicrobial layer. In one embodiment, the polymer coating includes a third layer of a dissolvable polymer disposed directly on the second layer of dissolvable polymer, and the third layer of dissolvable polymer has greater lubricity than the second layer of dissolvable material and is configured to dissolve in the human body prior to dissolution of the second layer of dissolvable polymer. As with above, in some embodiments the polymer coating provides beneficial properties to the metal housing, including improved tissue interface after implantation, enhanced tissue-electrode interface, improved anti-static properties, reduced wear, tear and scratches on the exterior surface during handling and assembly of the housing, antimicrobial benefits and very low friction surface.

One embodiment is a method of fabricating an implantable medical device including forming two halves of a housing, each half having an exterior surface. A first polymer coating including at least one layer of polymer material is disposed on the exterior surface of each half of the housing. In one embodiment, the first polymer coating includes a layer of dissolvable scratch resistant polymer material. In one embodiment, the method also includes completing fabrication of each half of the housing, dissolving the first polymer coating from each half of the housing, and applying a second polymer coating including at least one layer of polymer material on the exterior surface of each half of the housing, the at least one layer of polymer material including at least one layer of dissolvable scratch resistant polymer material. In one embodiment, the method includes installing internal components of the implantable medical device within the halves of the housing, coupling the housing halves together to form a single housing of the implantable medical device, completing fabrication of the implantable medical device, and dissolving the at least one layer of dissolvable scratch resistant polymer material from the housing of the implantable medical device.

Some of these provide beneficial properties to the metal housing, including improved tissue interface after implantation, enhanced tissue-electrode interface, improved anti-static properties, reduced wear, tear and scratches on the exterior surface during handling and assembly of the housing thereby avoiding manual polishing and buffing, advantages in manufacturing processing, antimicrobial benefits and very low friction surface.

FIG. 1 is a block and schematic diagram generally illustrating an example of a housing 32 of an implantable medical device 30, the housing 32 having an exterior surface 34 covered with a polymer coating 40 according to the present disclosure. Implantable medical device 30 may be one of any number of implantable devices, such as a cardiac pacemaker, a cardiac defibrillator, and a neurostimulator, for example. Typically, housing 32 is a metal case formed of a biocompatible material, such as titanium or a titanium alloy, for example, which defines a hermetically sealed interior space 42 in which device electronics 44 are disposed and protected from fluids of a body fluid side 46 external to housing 32 when device 30 is implanted in a body.

A header 48 attaches to housing 32 and includes a connector block 50 which typically includes one or more sockets for connecting to one or more sensing and/or stimulating leads 52 that extend between implantable medical device 30 and desired regions of the body, such as the human heart and brain, for example. A feedthrough device 54 establishes electrical pathways or connections through housing 32 that maintain the integrity of hermetically sealed interior space 42 and provide electrical connection of leads 52 to internal device electronics 44.

According to the present disclosure, polymer coating 40 includes at least one layer of polymer material and, as will be described in greater detail below, in some examples, may include multiple layers of polymer materials, with each layer being of a different polymer material. As will also be described in greater detail below, polymer coating 40, depending on the polymer material employed and how many layers of different polymer materials are included, provides housing 32 with one or more advantageous properties such as increased scratch protection/resistance, increased tissue adhesion after implantation, increased lubricity for easier insertion and/or removal from a body, and antimicrobial properties, for example. Additionally, as will be described below, depending on the function(s) to be provided by polymer coating 40, the layer or layers of polymer coating 40 may be provided and removed at different times during the manufacture of housing 32 and/or implantable medical device 30.

Figure 2:
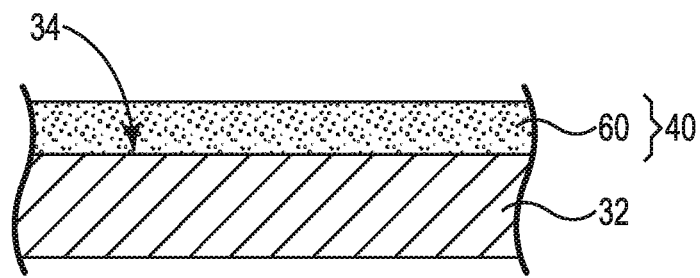
FIG. 2 is a cross-sectional view of a portion of a housing for an implantable having a polymer coating according to one embodiment.

For example, with reference to FIG. 2, which is a cross-sectional view of a portion of housing 32, according to one embodiment, polymer coating 40 includes a single layer 60 of a polymer material directly on the exterior surface 34 of housing 32. In one example, polymer layer 60 is a layer of conductive polymer material. Conductive polymer layer 60 provides several beneficial properties to metal housing 32 including improved tissue interface after implantation, enhanced tissue-electrode interface, and improved antistatic properties, for example.

Mechanical properties of conductive polymer layer 60, such as Young's modulus, for example, are much closer to those of body tissue than the metal of housing 32 and enable improved tissue integration with the implanted device. Such improved tissue integration reduces the occurrence of fibrous (non-vascularized) tissue formation about housing 32 after implantation in a body. Non-vascularized tissue reduces blood and oxygen flow to tissue and inhibits tissue healing at the implant site. It is known that well-vascularized tissue at the implant site is critical to healing trauma caused during implantation. By improving tissue integration and reducing the incidence of non-vascularized tissue, conductive polymer layer 60 improves the healing of tissue at the implant site.

According to one example, conductive polymer layer 60 also provides enhanced tissue-electrode interface between housing 32 and body tissue when implanted. For example, according to one embodiment, conductive polymer layer 60 is produced through the formation of nanoparticles which increases the effective surface area of the surface of housing 32 which has the effect of reducing interfacial impedance between housing 32 and body tissue. The reduced impedance enables improved sensing and signal detection when required, such as when housing 32 serves as an anode, for example.

Additionally, according to one example, conductive polymer layer 60 also serves as a lubricant which increases the lubricity of the housing 32. The increased lubricity provided by conductive polymer layer 60 increases the wear resistance of housing 32 and reduces the potential for abrasion of a lead body of a lead, such as leads 52 (see FIG. 1), as the body comes in contact with housing 32 after implantation.

According to one example, conductive polymers suitable for use as conductive polymer layer 60 include PEDOT, PolyPyrrole, Poly (N-methylpyrrole), Poly (hydroxymethyl-EDOT), Polyaniline, and Polythiophene, for example. Any number of conductive polymers that have been tested in vitro/in vivo for biomedical application may also be employed, including dopant added thereto for specific applications such as Heparin, Collgen, Fibrinogen, and PSS, for example.

Figure 3:
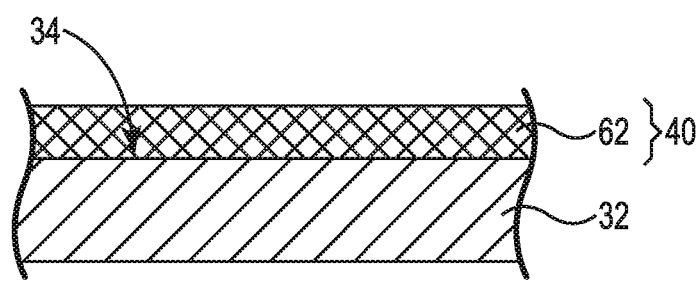
FIG. 3 is a cross-sectional view of a portion of a housing for an implantable having a polymer coating according to one embodiment.

As illustrated by FIG. 3, according to one embodiment, polymer coating 40 includes a single layer 62 of a dissolvable scratch resistant polymer material. According to one example, scratch resistant polymer layer 62 is applied to exterior surface 34 of housing 32 and reduces wear, tear and scratches on exterior surface 34 that would otherwise typically occur during handling and assembly of housing 32 and implantable medical device 30. According to one example, after assembly of implantable medical device 30 is completed, dissolvable scratch resistant polymer layer 62 is exposed to a bath, or to another suitable process, so that dissolvable scratch resistant polymer layer 62 dissolves and is washed away and removed from housing 32.

One or more applications of dissolvable scratch resistant polymer layer 62 may be employed during the manufacture and assembly of implantable medical device 30 and/or housing 32. For example, housing 32 is typically formed in two halves 32*a*, 32*b* (see FIG. 10*a* below) and can be manufactured using any number of processes including a stamping/drawing machine, metal injection molding, additive manufacturing, machining, superplastic forming, and liquid metal forming, for example. Housing 32 can be formed using any suitable material for implantable devices such as titanium, titanium alloys, niobium, cobalt/chromium allays, and stainless steel, for example. After electronics 44 and other internal components have been installed, the two halves 32*a*, 32*b* are joined together, such as by laser welding, for example. It is also common for housing 32 to be manufactured by a first party and to be shipped to a second party for assembly of implantable medical device 30.

According to one example, after initial formation of halves 32*a*, 32*b* of housing 32, such as by a first manufacturer, the exterior surface of each half of housing 32 is coated with a dissolvable scratch resistant polymer layer 62. Upon completion of the manufacture of housing halves 32*a*, 32*b* by the first manufacturer, the housing halves are shipped to a second manufacturer for assembly of medical device 30. According to one example, the initial dissolvable scratch resistant polymer layer 62 applied by the first manufacturer may remain in place during the assembly of implantable medical device 30 by the second manufacturer, including during the joining of the two halves 32*a*, 32*b* to form housing 32. Upon complete assembly of implantable medical device 30, the second manufacturer removes dissolvable scratch resistant polymer layer 62 from housing 32.

According to another example, the second manufacturer removes the initial dissolvable scratch resistant polymer layer 62 prior to laser welding together the two halves 32*a*, 32*b*. After the halves 32*a*, 32*b* are joined, the second manufacturer applies another dissolvable scratch resistant polymer layer 62 to exterior surface 34 of housing 32, which is not removed until final assembly of implantable medical device 30 has been completed.

By employing dissolvable scratch resistant polymer layer 62 according to the present disclosure, wear, tear, scratches, and abrasions to housing 32 can be greatly reduced or eliminated during manufacture of both housing 32 and implantable medical device 30. As such, use of dissolvable scratch resistant polymer layer 62 reduces or eliminates a manual polishing and buffing step that typically takes place at the end of both the manufacture of housing 32 and assembly of implantable medical device 30 to remove scratches/abrasions, etc., from housing 32. Such manual polishing and buffing step is time consuming and costly to the manufacture of housing 32 and implantable medical device 30.

According to one example, dissolvable polymer materials suitable for use as scratch resistant polymer layer 62 include Polyacrylic acid, polymethacrylic acid, polyethylene imine, Polyethelene oxide, water soluble cellulose acetate, Dextran, Chitosan, Polyvinyl alcohol, and polyacrlkimide, for example.

Figure 4:
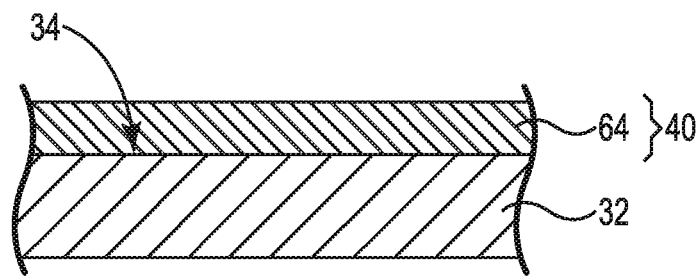
FIG. 4 is a cross-sectional view of a portion of a housing for an implantable having a polymer coating according to one embodiment.

As illustrated by FIG. 4, according to one embodiment, polymer coating 40 includes a single layer 64 of a dissolvable antimicrobial polymer material. According to one embodiment, dissolvable antimicrobial polymer layer 64 is applied to exterior surface 34 of housing 32 and remains on exterior surface after completion of the manufacture and assembly of implantable medical device 30. After implantation into a body, dissolvable antimicrobial polymer layer 64 is configured to dissolve after a desired time period (e.g. one hour) from exposure to bodily fluids and body temperature. Any bacteria that might have become attached to housing 34 is thereby washed from exterior surface 34 and is absorbed into the blood stream where such bacterial infections are readily treated with antibiotics. In contrast, if bacteria remains attached to housing 34 and forms a bio-film thereon, antibiotics are not as effective or may fail to work altogether to eliminate a resulting infection. As such, dissolvable antimicrobial polymer layer 64 acts as a bacteriostatic layer which prohibits the attachment of bacteria to and forming a biofilm on housing 32.

The polymer materials employed for dissolvable antimicrobial polymer layer 64 are bacteriostatic, meaning that they are not actively killing microbes, but work by preventing microbial adhesion to the surfaces of medical devices to which material is applied. When medical devices are handled or are implanted in the body, surgical site infection is a cause of concern as bacteria are attracted and can attach to the surface of a device housing. When dissolvable antimicrobial polymer layer 64 is employed, bacteria will attach to antimicrobial polymer layer 64 coating and will be unable to proliferate or form a biofilm as antimicrobial polymer layer 64 dissolves within a short period of time. Standard antibiotics are not able to deal with biofilms. However, without the formation of a biofilm, such bacteria operate in a planktonic fashion and the standard dose of antibiotic that is provided to the patient with the pacemaker implantation procedure is sufficient to deal with them.

According to one example, dissolvable polymer materials suitable for use as dissolvable antimicrobial polymer layer 64 include Polyacrylic acid, polymethacrylic acid, polyethylene imine, Polyethelene oxide, water soluble cellulose acetate, Dextran, Chitosan, Polyvinyl alcohol, and polyacrlkimide, for example.

Figure 5:
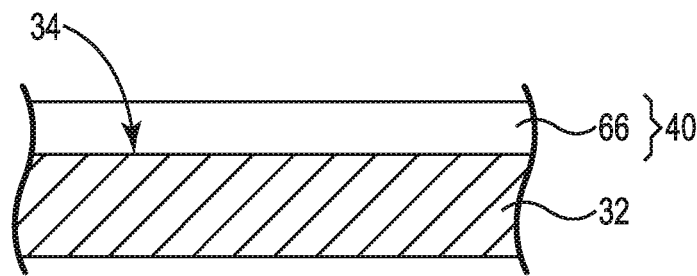
FIG. 5 is a cross-sectional view of a portion of a housing for an implantable having a polymer coating according to one embodiment.

As illustrated by FIG. 5, according to one embodiment, polymer coating 40 includes a single layer 66 of a dissolvable lubricious polymer material. According to one example, dissolvable lubricious polymer layer 66 is applied to exterior surface 34 of housing 32 where, upon contacting water or other fluids, such as bodily fluids, for example, lubricious polymer layer 66 is activated by absorbing water from such fluids and provides a very low friction surface for housing 34. According to one example, lubricious polymer layer 66 has a coefficient of friction in a range from 0.1-0.4, which enables implantable medical device 30 to be more easily inserted into a patient's body and results in less trauma to body tissue, thereby improving recovery time and reducing the development of non-vascular tissue in the implant area.

According to one example, polymer materials suitable for use as lubricious polymer layer 66 include Polyethylene oxide, Polyvinyl alcohol, any non-cross linked water soluble chitosan or hyalurnic acid, Polyvinyl pyrrolidone, among others, for example. It is noted that depending on the water soluble nature of the coating, the duration of the lubricity effect may vary.

Although illustrated above by FIGS. 2-5 as being of a single polymer layer, polymer 40 may include multiple layers of polymer materials, with each layer of polymer material being configured to provide a different advantageous property for housing 32 and implantable medical device 30.

Figure 6:
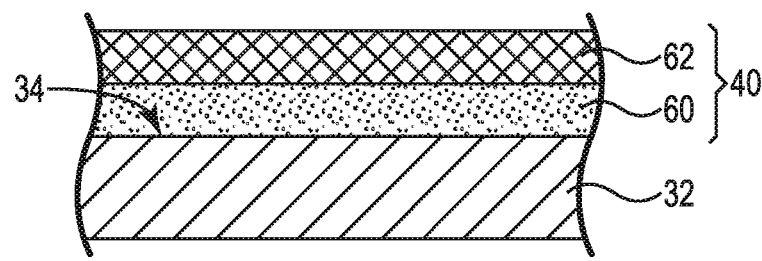
FIG. 6 is a cross-sectional view of a portion of a housing for an implantable having a polymer coating according to one embodiment.

For example, as illustrated by FIG. 6, according to one embodiment, polymer coating 40 includes conductive polymer layer 60 disposed directly on exterior surface 34 of housing 32, and dissolvable scratch resistant polymer layer 62 disposed on and covering conductive polymer layer 60. According to one embodiment, conductive polymer layer 60 and dissolvable scratch resistant polymer layer 62 are applied to the separate halves 32a, 32b of housing 34 prior to such halves being joined together (e.g. via laser welding), and remain on housing 32 throughout the manufacture and assembly of both housing 32 and implantable medical device 30. In another embodiment, conductive polymer layer 60 and dissolvable scratch resistant polymer layer 62 are applied to housing 32 after the separate halves 32a, 32b are joined together.

In both examples, upon completion of assembly of implantable medical device 30, a sterilization procedure is performed, at which time scratch resistant polymer layer 62 is removed (e.g. via a warm water bath) leaving conductive polymer layer 60 in place. Conductive polymer layer 60 then remains in place on exterior surface 34 of housing 32 and provides advantageous properties to implantable medical device 30 as described above with regard to FIG. 2.

Figure 7:
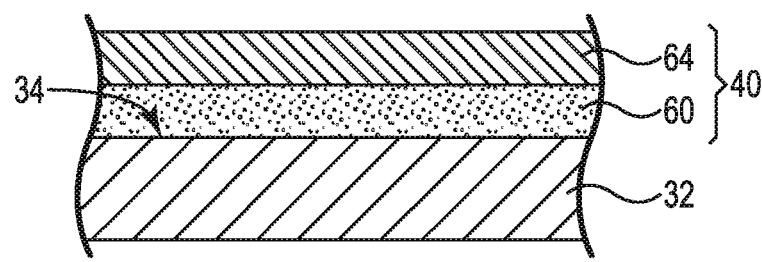
FIG. 7 is a cross-sectional view of a portion of a housing for an implantable having a polymer coating according to one embodiment.

As illustrated by FIG. 7, according to one embodiment, polymer coating 40 includes conductive polymer layer 60 disposed directly on exterior surface 34 of housing 32, and dissolvable antimicrobial polymer layer 64 disposed on conductive polymer layer 60. Upon implantation of implantable medical device 30, as described above with respect to FIG. 4, dissolvable antimicrobial polymer layer 64 dissolves after a desired time period from exposure to body temperatures and fluids, thereby flushing away any bacteria that may have attached to housing 34, and leaving conductive polymer layer 6 to provide advantageous properties as describe above with respect to FIG. 2.

According to one embodiment, conductive polymer layer 60 and dissolvable antimicrobial polymer layer 64 are applied to the separate halves 32a, 32b of housing 34 prior to such halves being joined together (e.g. via laser welding), and remain on housing 32 throughout the manufacture and assembly of both housing 32 and implantable medical device 30. In another embodiment, conductive polymer layer 60 and dissolvable antimicrobial polymer layer 64 are applied to housing 32 after the separate halves 32a, 32b are joined together.

In both examples, upon completion of the assembly of implantable medical device 30, a sterilization procedure is performed with dissolvable antimicrobial polymer layer 64 being configured so as to not be activated and dissolved by the sterilization procedure, thereby leaving both conductive polymer layer 60 and dissolvable antimicrobial polymer layer 64 disposed on exterior surface 34 of housing 32. Subsequently, as described above, upon implantation into a patient's body, dissolvable antimicrobial polymer layer 64 dissolves in response to body temperature and fluids to flush away potential bacteria, leaving conductive polymer layer 60 in place.

Figure 8:
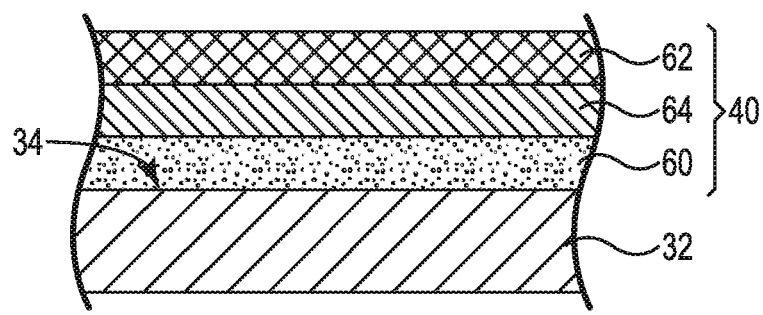
FIG. 8 is a cross-sectional view of a portion of a housing for an implantable having a polymer coating according to one embodiment.

As illustrated by FIG. 8, according to one example, polymer coating 40 includes conductive polymer layer 60 disposed directly on exterior surface 34 of housing 32, dissolvable antimicrobial polymer layer 64 disposed on conductive polymer layer 69, and dissolvable scratch resistant polymer layer 62 disposed on dissolvable antimicrobial polymer layer 64.

According to one embodiment, conductive polymer layer 60, dissolvable antimicrobial polymer layer 64, and dissolvable scratch resistant polymer layer 62 are applied to the separate halves 32a, 32b of housing 34 prior to such halves being joined together (e.g. via laser welding), and remain on housing 32 throughout the manufacture and assembly of both housing 32 and implantable medical device 30. In another embodiment, conductive polymer layer 60, dissolvable antimicrobial polymer layer 64, and dissolvable scratch resistant polymer layer 62 are applied to housing 32 after the separate halves 32a, 32b are joined together.

In both examples, upon completion of the assembly of implantable medical device 30, a sterilization procedure is performed during which dissolvable scratch resistant polymer layer 62 is dissolved and removed from housing 32. In contrast, dissolvable antimicrobial polymer layer 64 is configured so as to not be activated and dissolved by the sterilization procedure, thereby leaving both conductive polymer layer 60 and dissolvable antimicrobial polymer layer 64 disposed on exterior surface 34 of housing 32. Subsequently, as described above, upon implantation into a patient's body, dissolvable antimicrobial polymer layer 64 dissolves in response to body temperature and fluids to flush away potential bacteria, leaving conductive polymer layer 60 in place. Conductive polymer layer 60 then provides the advantageous properties as described above with respect to FIG. 2.

Figure 9:
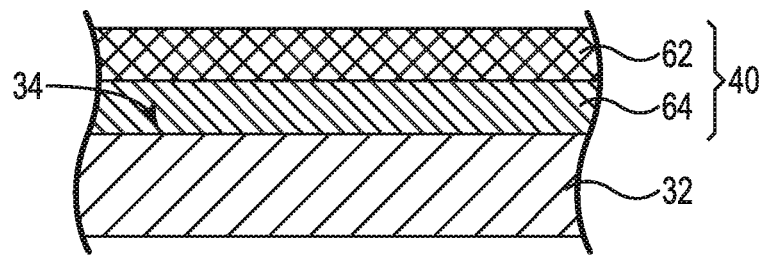
FIG. 9 is a cross-sectional view of a portion of a housing for an implantable having a polymer coating according to one embodiment.

As illustrated by FIG. 9, according to one embodiment, polymer coating 40 includes dissolvable antimicrobial polymer layer 64 disposed directly on exterior surface 34 of housing 32, and dissolvable scratch resistant polymer layer 62 disposed on dissolvable antimicrobial polymer layer 64.

According to one embodiment, dissolvable antimicrobial polymer layer 64 and dissolvable scratch resistant polymer layer 62 are applied to the separate halves 32*a*, 32*b* of housing 34 prior to such halves being joined together (e.g. via laser welding), and remain on housing 32 throughout the manufacture and assembly of both housing 32 and implantable medical device 30. In another embodiment, dissolvable antimicrobial polymer layer 64 and dissolvable scratch resistant polymer layer 62 are applied to housing 32 after the separate halves 32*a*, 32*b* are joined together.

In both examples, upon completion of the assembly of implantable medical device 30, a sterilization procedure is performed during which dissolvable scratch resistant polymer layer 62 is dissolved and removed from housing 32. In contrast, dissolvable antimicrobial polymer layer 64 is configured so as to not be activated and dissolved by the sterilization procedure, thereby leaving dissolvable antimicrobial polymer layer 64 disposed on exterior surface 34 of housing 32. Subsequently, as described above, upon implantation into a patient's body, dissolvable antimicrobial polymer layer 64 dissolves in response to body temperature and fluids to flush away potential bacteria.

Although not illustrated, according to other embodiments, the function of dissolvable scratch resistant layer 62 and that of dissolvable antimicrobial polymer layer 64 can be combined in a single dissolvable polymer layer. According to such embodiment, a single layer 62/64 of dissolvable polymer material provides both the scratch resistant and antimicrobial functions and dissolves in a desired time period after implantation into a patient's body.

FIGS. 10*a*-10*g* generally illustrate a process for fabricating an implantable medical device, such as implantable medical device 30, having a housing employing a polymer coatings on the exterior surface thereof, according to the present disclosure, such as polymer coating 40 on the exterior surface 34 of housing 32.

Figure 10A:
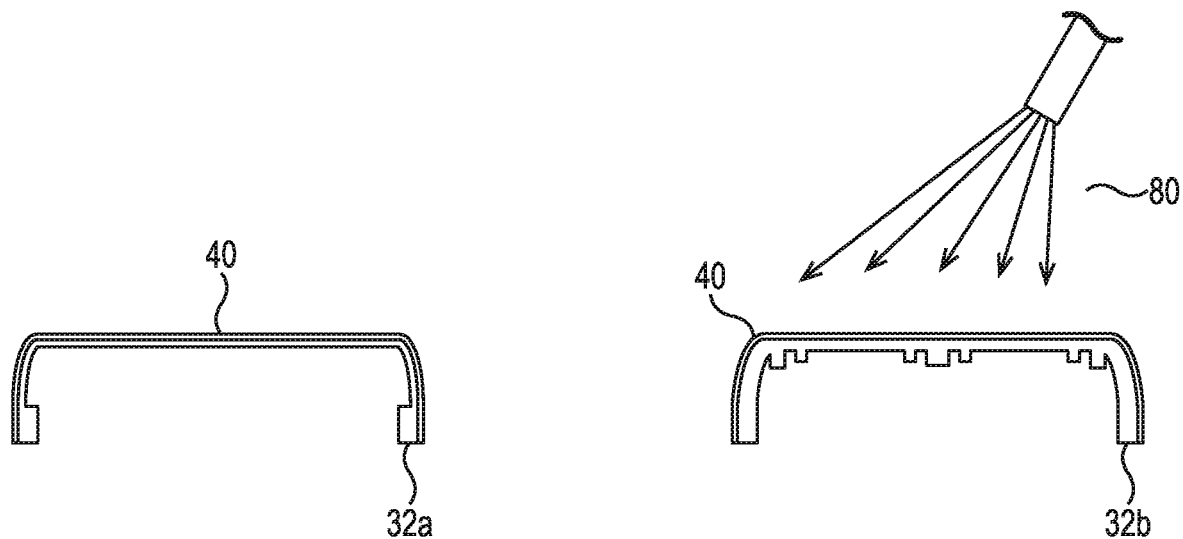
FIGS. 10a-10g illustrate an example fabrication process employing polymer coatings according to the present disclosure

As illustrated by FIG. 10*a*, fabrication begins with the formation of housing 32. In one embodiment, housing 32 is formed in two halves 32*a*, 32*b*, with halves 32*a*, 32*b* being formed using any number of processes, or combination of processes, such as stamping/drawing, metal injection molding, additive manufacturing, machining, superplastic forming, and liquid metal forming, for example. Housing 32 can be formed using any suitable material for implantable devices such as titanium, titanium alloys, niobium, cobalt/chromium allays, and stainless steel, for example.

In one example, after an initial formation process, the exterior surfaces 34 of halves 32*a*, 32*b* are coated with a polymer coating 40 according to the present disclosure. According to one embodiment, polymer coating 40 is applied via spray coating process, as illustrated generally at 80. Polymer coating 40 can be deposited using any suitable conventional coating process such as spray coating, dip coating, melt extrusion, brush coating, and solution casting, for example. Typical coating thicknesses for each of the one or more layers forming polymer coating 40 range from 10 to 100 microns. However, other layer thickness may be employed.

Figure 10B:
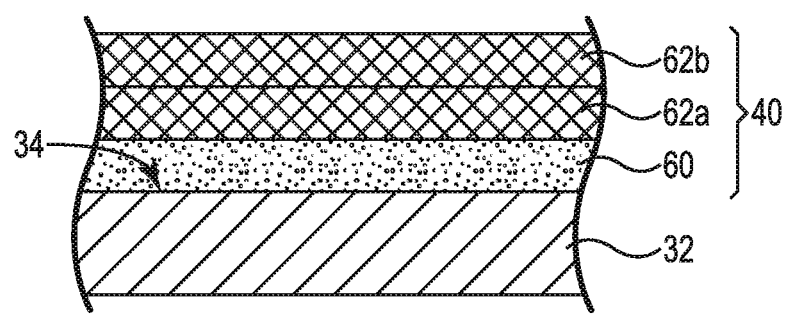

According to one embodiment, as illustrated by FIG. 10*b*, polymer coating 40 includes a conductive polymer layer 60 disposed directly on exterior surfaces 34 of housing halves 32*a* and 32*b*, a first dissolvable scratch resistant polymer layer 62*a* disposed on conductive polymer layer 62*a*, and a second dissolvable scratch resistant polymer layer 62*b* disposed on first dissolvable scratch resistant polymer layer 62*a*. Each of the polymer layers 60, 62*a*, and 62*b* are successively deposited on housing halves 32*a* and 32*b* using one or a combination of suitable traditional coating methods.

According to the present example, as illustrated by FIG. 10*b*, polymer coating 40 is a multilayer coating. According the present disclosure, different dissolvable polymer layers, such as first scratch resistant polymer layer 62*a* and a second scratch resistant polymer layer 62*b* can be configured or "programmed" to dissolve at different rates and under different conditions. For example, according to embodiment, topmost scratch resistant polymer layer 62*b* may be configured to dissolve in a bath of isopropyl alcohol (IPA), while the underlying first scratch resistant polymer layer 62*a* may be configured to dissolve in a bath of room temperature water.

In embodiments, such as where coating 40 includes three layers of dissolvable polymer, a topmost polymer layer (e.g. a first scratch resistant polymer layer) may be configured to dissolve in a bath of room temperature water, a second dissolvable polymer layer directly underlying the topmost dissolvable polymer layer (e.g. a second scratch resistant polymer layer) may be configured to dissolve when washed in a bath of isopropyl alcohol (IPA), and a third layer of dissolvable polymer material directly underlying the second dissolvable polymer layer (e.g. a dissolvable antimicrobial layer 64) may be configured to dissolve in bodily fluids, including water, at body temperatures (e.g. approximately 37° C.).

Figure 10C:
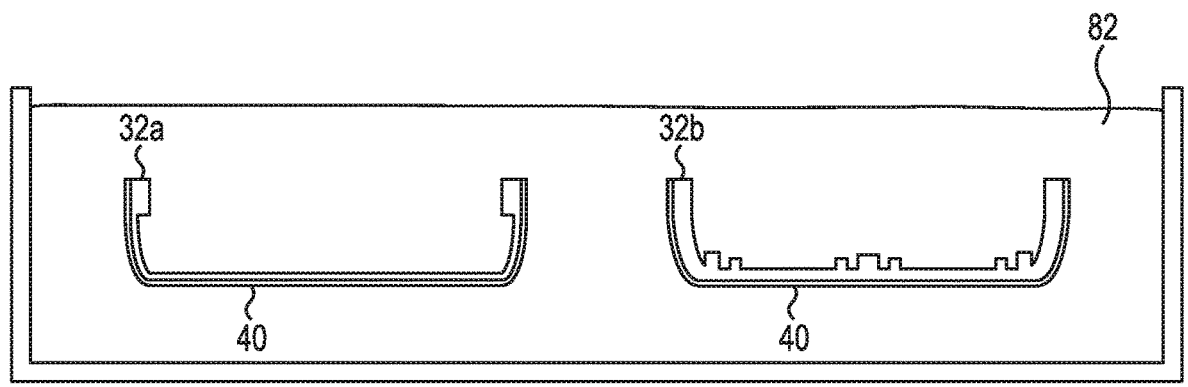
Figure 10D:
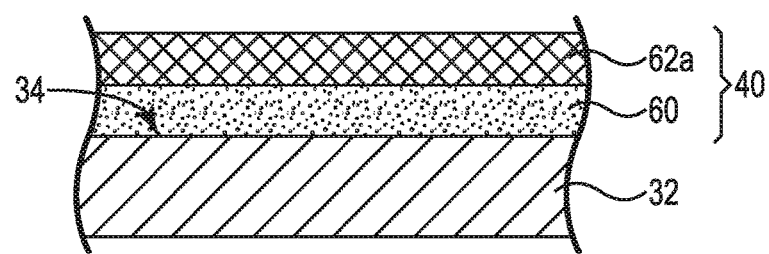

Returning to the present example, with reference to FIG. 10*c*, according to one example, after final processing of the first and second halves 32*a*, 32*b* is completed, first and second halves 32*a*, 32*b* are placed in a bath of isopropyl alcohol 82 to remove second scratch resistant polymer layer 62*b*. After removing second scratch resistant polymer layer 62*b*, polymer coating is as illustrated in FIG. 10*d*. In one example, the second scratch resistant polymer layer 62*b* is removed by the first manufacturer (i.e. the manufacturer of housing 32), who then sends first and second halves 32*a*, 32*b* of housing 32 having polymer coating 40 as illustrated by FIG. 10*d* to a second manufacturer for fabrication of implantable medical device 30.

Figure 10E:
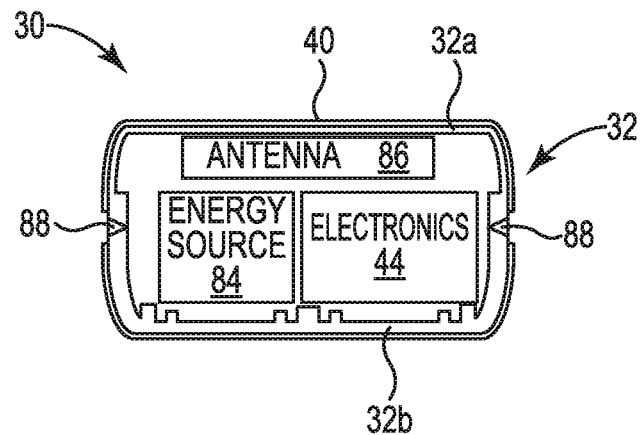

With reference to FIG. 10*e*, during processing by the second manufacturer, electronics 44 and other internal components, such as an energy source 84 and antenna 86 are installed and halves 32*a*, 32*b* are joined together, such as via laser welding, as indicated by laser welds 88, to form housing 32.

Figure 10F:
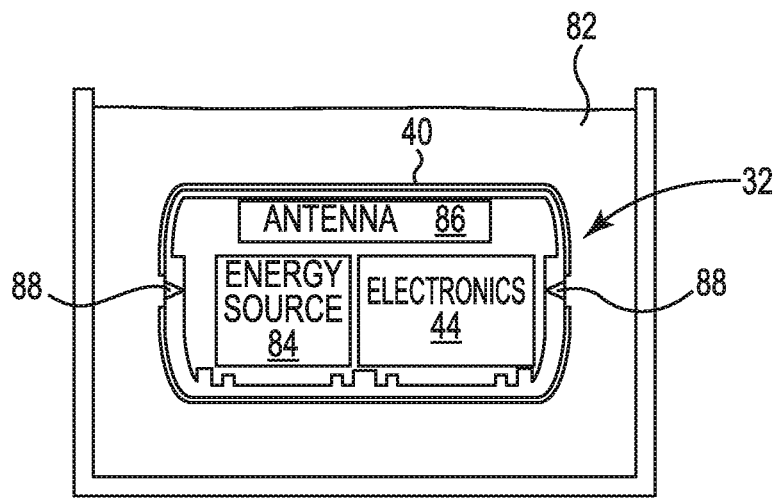
Figure 10G:
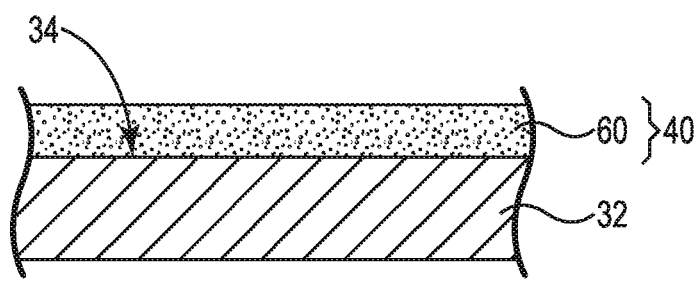

As illustrated by FIG. 10*f,* upon completion of the manufacture and assembly of implantable medical device 30, the first dissolvable scratch resistant polymer layer 62*a* is dissolved from exterior surface 34 of housing 32 using a room temperature water bath 90. After removing first scratch resistant polymer layer 62*b*, polymer coating is as illustrated in FIG. 10*d*. The resulting implantable medical device 30 is then subjected to a sterilization process prior to packaging.

As described above, when polymer coating 40 is a multilayer coating, such as illustrated by FIG. 8, for example, different dissolvable polymer layers, such as scratch resistant polymer layer 62 and antimicrobial polymer layer 64, can be configured or "programmed" to dissolve at different rates and under different conditions. For example, according to one embodiment, the outermost scratch resistant polymer layer 62 can be configured to dissolve in a bath of room temperature water, for example, while the middle layer 64 of antimicrobial polymer material can be configured to dissolve in bodily fluids, including water, at body temperatures (e.g. approximately 37° C.).

In another embodiment, a topmost scratch resistant polymer layer (e.g. scratch resistant polymer layer 62b of FIG. 10) may be configured to dissolve in a bath of room temperature water, a second scratch resistant polymer layer directly underlying the topmost scratch resistant polymer layer (e.g. scratch resistant polymer layer 62a directly underlying scratch resistant polymer layer 62b in FIG. 10) may be configured to dissolve when washed in a bath of isopropyl alcohol (IPA), and a third layer of dissolvable polymer material directly underlying the second scratch resistant polymer layer, such as dissolvable antimicrobial layer 64, may be configured to dissolve in bodily fluids, including water, at body temperatures (e.g. approximately 37° C.).

Any number of conventional techniques can be employed to "program" different dissolvable polymer material layers to dissolve under different conditions and at different rates. For example, in some embodiments, poly acrylic acid (PAA) may be employed as a polymer material for one of the dissolvable polymer layers. PAA is typically highly soluble in water and dissolves quickly. In one example, the solubility time of PAA can be extended by modifying the side chains of PAA which contain (Na+)-carboxylate groups. The Na+ ions can be exchanged with calcium ions to produce a water insoluble PAA-$Ca_2$+ polymer by soaking the PAA film in an aqueous $CaCl_2$ solution. The resulting coating is stable in water for a longer duration, such as up to 30 to 60 minutes depending on properties of the $CaCl_2$ solution.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A housing for an implantable medical device comprising:
   a hermetically-sealed metal case having an external surface; and
   a polymer coating disposed on the external surface of the metal case;
   wherein the polymer coating comprises an inner layer and a topmost layer of a polymer material, wherein the topmost layer is configured to dissolve at a first temperature and the wherein the inner layer, which is under the topmost layer, is configured to dissolve at a second temperature that is different from the first temperature.

2. The housing of claim 1, wherein the inner layer of polymer material comprises a conductive polymer material.

3. The housing of claim 1, wherein the topmost layer of polymer material comprises a dissolvable polymer material.

4. The housing of claim 1, wherein the topmost layer of polymer material comprises a dissolvable scratch resistant polymer material.

5. The housing of claim 1, wherein the inner layer of polymer material comprises a dissolvable antimicrobial polymer material.

6. The housing of claim 1, wherein the polymer coating comprises one or more inner layers of polymer material disposed under the topmost layer of polymer material, wherein each inner layer is configured to dissolve at a different temperature.

7. The housing of claim 1, wherein the inner layer of polymer material comprises a conductive polymer material, wherein topmost layer of polymer material comprises a dissolvable polymer material, wherein the first temperature is room temperature, and wherein the second temperature is body temperature.

8. An implantable medical device comprising:
   a hermetically-sealed metal housing defining an interior space and having an external surface;
   a polymer coating disposed on and covering the external surface of the metal housing;
   wherein the polymer coating comprises a first, a second and a third layer of a polymer material, wherein the third layer is an outermost layer that is configured to dissolve at room temperature and the wherein the second layer, which is under the third layer, is configured to dissolve at body temperature.

9. The implantable medical device of claim 8, wherein the first layer of polymer material comprises a conductive polymer disposed directly on the external surface of the metal housing.

10. The implantable medical device of claim 9, wherein the polymer coating comprises the second layer of a dissolvable polymer disposed directly on the first layer of conductive polymer.

11. The implantable medical device of claim 10, wherein the second layer of dissolvable polymer comprises an antimicrobial layer.

12. The implantable medical device of claim 10, wherein the third layer of a dissolvable polymer is disposed directly on the second layer of dissolvable polymer, wherein the third layer of dissolvable polymer has greater lubricity than the second layer of dissolvable material and is configured to dissolve in the human body prior to dissolution of the second layer of dissolvable polymer.

* * * * *